(12) United States Patent
Guimera Brunet et al.

(10) Patent No.: US 8,948,840 B2
(45) Date of Patent: Feb. 3, 2015

(54) NON-INVASIVE SENSOR FOR DETERMINING FUNCTIONAL CHARACTERISTICS OF THE CORNEA, DEVICE INCLUDING SAID SENSOR AND USE THEREOF

(75) Inventors: Antón Guimera Brunet, Barcelona (ES); Rosa Villa Sanz, Barcelona (ES); Gemma Gabriel Buguña, Barcelona (ES); Miguel José Maldonado López, Valladolid (ES)

(73) Assignees: Consejo Superior de Investigaciones Cientificas, Madrid (ES); Universidad de Valladolid, Valladolid (ES)

( * ) Notice: Subject to any disclaimer, the term of this patent is extended or adjusted under 35 U.S.C. 154(b) by 0 days.

(21) Appl. No.: 13/581,994

(22) PCT Filed: Feb. 28, 2011

(86) PCT No.: PCT/ES2011/070131
§ 371 (c)(1),
(2), (4) Date: Sep. 26, 2012

(87) PCT Pub. No.: WO2011/107645
PCT Pub. Date: Sep. 9, 2011

(65) Prior Publication Data
US 2013/0012803 A1    Jan. 10, 2013

(30) Foreign Application Priority Data
Mar. 2, 2010   (ES) .................................. 201030307

(51) Int. Cl.
*A61B 5/053*   (2006.01)
*A61B 5/00*    (2006.01)

(52) U.S. Cl.
CPC ............... *A61B 5/053* (2013.01); *A61B 5/6821* (2013.01); *A61B 5/0537* (2013.01); *A61B 2562/0209* (2013.01); *A61B 2562/043* (2013.01); *A61B 2562/166* (2013.01)
USPC ......................................... 600/383; 600/547

(58) Field of Classification Search
CPC ................. A61B 5/053; A61B 5/6821; A61B 2562/043; A61B 2562/0209; A61B 2562/166
USPC .................................................... 600/383, 547
See application file for complete search history.

(56) References Cited

U.S. PATENT DOCUMENTS 4,386,831 A * 6/1983 Grounauer .................... 351/205
4,874,237 A * 10/1989 Cringle ......................... 600/383
(Continued)

FOREIGN PATENT DOCUMENTS

CN    101766473 A    7/2010
ES    2 324 189       7/2009

OTHER PUBLICATIONS

Benvenuto, A., "Impedance Microprobes for Myocardial Ischemia Monitoring", 1$^{st}$ Annual International IEEE-EMBS Special Topic Conference on Microtechnologies in Medicine & Biology, 2000, pp. 1-5.
(Continued)

*Primary Examiner* — Lee S Cohen
(74) *Attorney, Agent, or Firm* — Gary J. Gershik; Cooper & Dunham LLP

(57) ABSTRACT

The present invention relates to a sensor and device incorporating said sensor for obtaining data useful to determine the functional characteristics of the cornea in a non-invasive manner, particularly for establishing a correlation between the impedance at different frequencies and the permeability of the endothelium and epithelium and stromal hydration level.

18 Claims, 5 Drawing Sheets

(56) References Cited

U.S. PATENT DOCUMENTS

| | | | |
|---|---|---|---|
| 7,596,400 B2* | 9/2009 | Valjakka et al. | 600/383 |
| 8,118,752 B2* | 2/2012 | Hetling et al. | 600/558 |
| 8,355,768 B2* | 1/2013 | Masmanidis et al. | 600/378 |
| 2011/0046509 A1* | 2/2011 | Uematsu et al. | 600/547 |
| 2011/0184271 A1* | 7/2011 | Veciana et al. | 600/398 |

OTHER PUBLICATIONS

Biermann, H. et al., "Messung der elektrischen Impedanz an normalen und pathologischen Hornhäuten", Fortschritte der Ophthalmologie (including English translation and abstract), 1991, vol. 88, pp. 17-20.

Guimera, A. et al., "Non-invasive assessment of corneal endothelial permeability by means of electrical impedance measurements", Medical Engineering and Physics, 2010, vol. 32, pp. 1107-1115.

Ivorra, A. et al., "Minimally invasive silicon probe for electrical impedance measurements in small animals", Biosensors and Bioelectronics, 2003, vol. 391, pp. 391-399.

Watanabe, M. et al., "Dielectric Measurements on the Rabbit Cornea Using a Surface Electrode", Journal of Japanese Ophthalmological Society, 1993, vol. 97, pp. 569-574 (including English translation).

International Search Report issued by the International Searching Authority (ISA/O.E.P.M.) on Jul. 27, 2011 in connection with International Application No. PCT/ES2011/070131.

Biermann, H. et al., "Messung der elektrichen Impedanz an normalen und pathologischen Hornhäuten", Fortschritte der Ophthalmologie (including summary in English Language), 1991, vol. 88, pp. 17-20.

Watanabe, M. et al., "Dielectric Measurements on the Rabbit Cornea Using a Surface Electrode", Journal of Japanese Ophthalmological Society, 1993, vol. 97, pp. 569-574.

Mitsubayashi, K. et al., "Flexible Conductimetric Sensor" Analytical Chemistry, American Chemical Society, US, vol. 65, No. 24, pp. 3586-3590.

Oct. 7, 2014 Japanese Office Action, issued in connection with counterpart Japanese Patent Application No. 2012/555452 (including English language translation).

Japanese Patent JP 6-502323 granted Mar. 17, 1994, and corresponding to English language counterpart PCT International Patent Application Publication No. WO 92/06634, Centrum For Dentalteknik Och Biomaterial, published Apr. 30, 1992.

* cited by examiner

NON-INVASIVE SENSOR FOR DETERMINING FUNCTIONAL CHARACTERISTICS OF THE CORNEA, DEVICE INCLUDING SAID SENSOR AND USE THEREOF

RELATED APPLICATIONS

This application is a §371 national stage of PCT International Application No. PCT/ES2011/070131, filed Feb. 28, 2011, claiming priority of Spanish Patent Application No. P201030307, filed Mar. 2, 2010, the contents of each of which are hereby incorporated by reference into this application.

OBJECT OF THE INVENTION

The object of the present invention relates to a sensor and a device incorporating said sensor for obtaining useful data for diagnosing the state of the cornea in a non-invasive manner.

More specifically it is a device which allows measuring the impedance of the cornea at different frequencies to establish a correlation between impedance and permeability of the endothelium and epithelium and stromal hydration level, to thus determine the functional characteristics of the cornea,

BACKGROUND OF INVENTION

The cornea is the transparent hemispherical structure located in front of the eye, which allows the passage of light and protects the iris and lens. It has the shape of a concave disc with an average diameter of 11.5 mm in humans and it possesses significant refractive optic properties, providing approximately 70% of the total focusing ability of the eye.

The cornea consists of three layers: the outermost layer is the corneal epithelium composed of pluri-stratified non-keratinized epithelium with an enormous regenerative potential; the intermediate layer is the stroma, the widest layer of the three; and the mono-stratified endothelium is the innermost layer consisting of one single layer of cells. Two membranes separating the stroma from the other two corneal layers are distinguished: Descemet's membrane separating the stroma from the endothelium and Bowman's membrane separating the stroma from the epithelium.

The epithelium represents 10% of the total thickness of the cornea (approximately 550 microns in humans (and is formed by several layers of cells acting as a protective barrier against external agents. The transport of ions through cells of the epithelial layer is one of those responsible for regulating corneal functionality.

The stroma is formed in humans by 200 to 250 sheets of collagen fibers arranged parallel to the corneal surface. The stroma is ultimately responsible for the biomechanical properties of the cornea, as well as its curvature and transparency. To maintain its transparency it does not have capillaries for nourishing the cornea, such that nutrients are supplied through the epithelium and endothelium. On the other hand, the degree of stromal hydration is directly related to the transparency of the cornea, remaining in a constant state of dehydration.

The endothelium consists of a monolayer of cuboidal cells forming a hexagonal mosaic and maintains the transparency of the tissue by controlling stromal hydration. On one hand, there is a flow by diffusion between endothelial cells controlled by the junctions between them (tight junctions). On the other hand, endothelial cells are specialized in pumping water from the stroma to the aqueous humour, creating an active flow through the fluidic pump and ensuring the homeostasis of the cornea. A feature of the corneal endothelium, unlike the epithelium, is its inability for cell renewal. This causes a loss of cell population with age as well as a decrease in their thickness since the cells are forced to cover the entire posterior corneal surface, leading to a loss of its ability to control stromal hydration level as a result. This aging can occur in an exaggerated manner in dystrophies and as a result of disease, eye surgery or use of ophthalmic drugs.

FIG. 1 shows the different layers making up the cornea, as well as the main mechanisms for controlling the stromal hydration level: diffusion through the epithelium, diffusion and pumping through the endothelium. Although the study of the permeability of these layers is of great clinical interest, so far only studies based on in vitro measurements, usually with tissues removed and placed in a specific sensor device, have been conducted. There are also some studies that take in vivo measurements in animals, but using highly invasive methods, which usually involves the impairment of the tissue for further studies and the impossibility to do so in a clinic with patients. In clinical practice the measurement of the thickness of the cornea (pachymetry) is often used as an indirect measurement for corneal dysfunction.

The study of passive electrical properties of the different layers of the cornea is commonly used in in vitro studies to evaluate their permeability. But the methods used in these studies are not applicable to in vivo measurements. Cellular and acellular media have a different behavior to electric current. In general, the tissues are composed of cells embedded in an extracellular medium. At low frequencies, <1 kHz, the current is distributed in the extracellular medium (essentially an ionic solution with resistive behavior), while at higher frequencies, >100 kHz the current is capable of passing through cell walls and intracellular medium (the behavior of the membranes is capacitive and the intracellular medium is resistive). FIG. 2 graphically depicts this difference in behavior as a function of frequency. Based on this behavior of biological tissues the status of the different layers of the cornea can be analyzed using measurements based on its passive electrical properties, such as is the case of impedance measurements.

DESCRIPTION OF THE INVENTION

The present invention provides a sensor for measuring the impedance, useful for determining the functional characteristics of the cornea, as well as a device comprising said sensor.

Therefore, a first aspect of the invention relates to an impedance measuring sensor comprising n microelectrodes, n being comprised between 4 and 30, said microelectrodes being arranged on a substrate, the size and arrangement of the microelectrodes being suitable so that they contact a cornea simultaneously, and wherein the microelectrodes are selected for taking the measurement in groups of 4 by way of 2 external microelectrodes and 2 internal microelectrodes.

A second aspect of the present invention relates to an impedance measuring device comprising a sensor as described above and a multi-frequency impedance measuring equipment connected either physically by wires or by telemetry to said sensor.

A third aspect of the invention relates to the use of a sensor or a device comprising said sensor as described above for measuring impedance to determine the functional characteristics of the cornea The term "microelectrodes" refers to microelectrodes that only require contact with the surface of the cornea to measure the impedance. On the other hand, the expression "suitable size and configuration so that they contact a cornea simultaneously" means that in order to successfully measure the impedance, all microelectrodes used must make electrical contact with the cornea, which implies constraints on size and relative arrangement of the microelectrodes.

To take a measurement, the sensor of the invention is connected to the impedance measuring equipment. These devices work by injecting an electric current in the medium the impedance of which is to be measured through the microelectrodes, the resulting electrical potential being simultaneously obtained through other microelectrodes. The impedance of the tissue is calculated from this data.

It has been proven that permeability increases in endothelial and epithelial layers, which are formed by cells, are normally due to the increase in intercellular spaces or decrease in the number of cells, which causes a decrease in impedance. This increase in the permeability of the endothelial and epithelial layers in turn causes an increase in stromal hydration, which also results in a decrease in impedance due to an increase in ionic concentration.

The impedance measuring equipment incorporates means for injecting a variable frequency electric current in the cornea and means for simultaneously reading the resulting potential, thus obtaining data of the tissue impedance for a multi-frequency measurement in the range of 10 Hz to 1 MHz.

Measurements taken in different frequency ranges and with the suitable microelectrodes give rise to impedance values that allow obtaining conclusions about the functional status of the different layers of the cornea.

It has been observed that in the case of frequency<1 kHz the measured conductivity depends primarily on the conductivity of the epithelial layer. Due to its low conductivity at low frequencies, the amount of electrical current that can pass through it is virtually zero, so that the voltage drop recorded depends on the conductivity of the corneal epithelium.

In the range of 1 kHz<frequency<100 KHz, the analysis of the impedance measurement is more complex since it involves several factors. The conductivity of the cell layers (epithelium and endothelium) is two orders of magnitude greater than that of the rest of the layers, allowing the passage of a significant amount of current to the acellular layers (stroma and aqueous humor). On the other hand, the conductivity of aqueous humor is higher than that of the stroma, so electrical current will tend to move through this layer. The amount of current that can cross the endothelium and circulate with the aqueous humor is directly related to the conductivity of the endothelium, as well as with its permeability. Consequently, if the current circulating through the aqueous humor increases, the recorded impedance decreases, which indicates an increase in endothelial permeability.

In the frequency>100 kHz range electrical current is capable of passing through cells, such that the impedance measurement depends on the conductivity of the stroma and of the aqueous humor because they are the larger layers. The conductivity of aqueous humor can be considered constant, such that variations in the measured impedance are related to variations in the conductivity of the stroma, and these in turn to their degree of hydration.

In a particular embodiment of the invention, the microelectrodes are arranged in a planar manner on the substrate.

In another particular embodiment of the invention, the sensor comprises 10 microelectrodes.

The conductive microelectrodes can be made of metal or non-metal material, preferably a biocompatible material.

In a particular embodiment of the invention, the microelectrodes are made of metal material selected from gold, platinum, nickel, aluminum, titanium, titanium nitride, chromium and possible alloys thereof;

In another particular embodiment of the invention, the microelectrodes are made of non-metal material selected from carbon nanotubes, graphene and conductive polymers.

These microelectrodes can be modified by means of processes that improve their performance. Therefore, for example, carbon nanotubes may be deposited or black platinum or gold be electro-deposited to improve contact with the tissue and hydrogels such as polyhydroxymethylmethacrylate (pHEMA) can be deposited to stabilize the above processes.

In another particular embodiment of the invention, said microelectrodes have an elongated shape and are arranged in parallel according to their longest side, the microelectrodes being configured either to inject an electric current or else to measure a potential.

On the other hand, the substrate on which the microelectrodes are arranged is made up of a biocompatible material and can be rigid or flexible, preferably transparent which allows the person taking the measurement to observe if the microelectrodes are contacting the surface of the cornea. Likewise, a rigid substrate may be essentially flat or have an angle of curvature which allows its adaptation to the surface of the cornea. In the case of a rigid substrate, the material is selected from silicon, silicon carbide, glass and PCB (printed circuit board, RF4). In the case of a flexible substrate, the material is selected from polymers such as: SU8, polymethylmethacrylate (PMMA), polydimethylsiloxane (PDMS), polyimide, polyethylene naphthalate (PEN), polyethylene terephthalate (PET), polystyrene, cycloolefin polymer (COP) and polycarbonate.

In a particular embodiment of the invention, the substrate is rigid and the microelectrodes are 2 mm in length and 0.3 mm in width.

In another particular embodiment of the invention, the substrate is flexible and the microelectrodes are 1 mm in length and 0.3 mm in width.

FIG. 3A shows a diagram of the different layers defining the sensor, the substrate and the microelectrodes.

The sensor may be adapted in different ways for its implementation to take impedance measurements. The possibility of manufacturing a lens-shaped sensor, adapting the sensor to a carrier or to a container that can contain isolated corneas is contemplated.

It has also been proven that the measured impedance values depend on the geometry of the microelectrodes used. Likewise the contribution of the electrical properties of each layer of the cornea to the total measured impedance is different. It can be said that the layers closer to the microelectrodes have a higher sensitivity, such that a variation in their electrical properties will cause a greater change in the total impedance. Therefore, the depth of the measurement taken depends on the relative distance between the microelectrodes.

The sensor of the present invention has the advantage that the impedance measurement of the cornea at different frequencies to establish a correlation between the impedance and permeability of the endothelium and epithelium and stromal hydration level can be determined with the use of the same sensor described above by conveniently combining four microelectrodes of the several present in the sensor, since it allows modulating the amplitude of the relative distance between them. Therefore, FIG. 3B shows how the use of different microelectrodes allows determining the permeability of the different layers of the cornea. The design and use of microelectrodes meets certain parameters.

The maximum and minimum values of the parameters defining the geometry of the microelectrodes are indicated below and the optimal values so that the sensor detects changes in the three main layers of the cornea are provided. FIG. 4 outlines these parameters in a sensor formed by ten microelectrodes. In this case the microelectrodes are of the same length and width and are arranged parallel with 2 external microelectrodes (I+, I−) and 2 internal microelectrodes (V+, V−), the arrangement of the microelectrodes as external microelectrodes (V+, V−) and 2 internal microelectrodes (I+, I−), also being feasible. See FIG. 5.

The parameters are:

We is the width of each electrode and is comprised between 0.03 mm and 1 mm, preferably being 0.3 mm, Le is the length of the electrode, and is comprised between 0.03 mm and 11 mm, preferably being 1 mm or 2 mm, Ws is the width of the assembly of electrodes selected for taking the measurement or the distance between the middle lines of the external microelectrodes and is comprised between 0.2 mm and 11 mm. The preferred value of this parameter depends on the layer on which information is to be obtained, preferably being 5 mm in the case of endothelial layer, 1 mm in the case of epithelium and 1.8 mm in the case of stroma.

Nre is the ratio of microelectrode gap where Nre=Sei/Se, wherein Sei is the distance between the middle lines of the internal microelectrodes and Be is the distance between the middle lines of an internal electrode and the closest external electrode, and is comprised between 20 and 0.1, preferably being 3.

On the other hand it has been proven that by varying the width of the sensor Ws the sensor sensitivity to a particular layer varies, since this parameter determines the depth of the measurement. By varying the width of the sensor the frequency ranges detailed above are slightly altered, moving to higher frequencies by reducing the width of the sensor.

For sensors with width Ws>3 mm variations in the three layers of the cornea can be detected.

For sensors with width 1.5 mm<Ws<3 mm variations in the stroma and the epithelium can be detected, being the optimum range for detecting changes in the conductivity of the stroma.

For sensors with width Ws<1.5 mm only variations in the epithelial layer can be detected.

As detailed above, the functional status of each layer of the cornea correlates with the impedance measurement of the cornea depending on the width of the selected electrode assembly (Ws) and the frequency at which the measurement is taken. Therefore, the following table summarizes the values of these two parameters for the case of each layer of the cornea.

|  | Epithelium | Endothelium | Stroma |
|---|---|---|---|
| Ws | Ws < 1.5 mm | Ws > 3 mm | 1.5 mm < Ws < 3 mm |
| Frequency | Freq < 1 kHz | 1 kHz < Freq < 100 kHz | Freq > 100 kHz |

DESCRIPTION OF A PREFERRED EMBODIMENT

Figure 1:
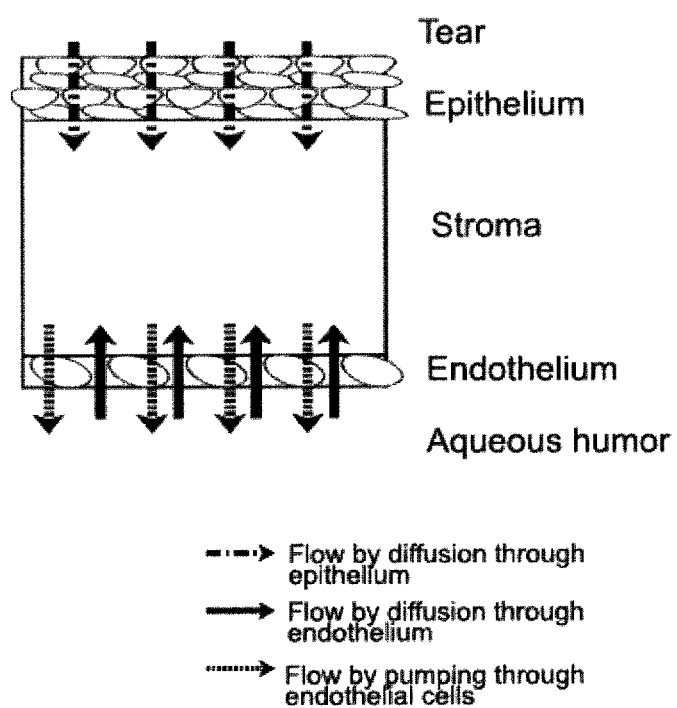
FIG. 1 schematically shows the different layers forming the cornea (the tears, the cell epithelium, the acellular stroma, the cell endothelium and the aqueous humor) and the main mechanisms for controlling stromal hydration level. Solid line shows the flow by diffusion of aqueous humor to the stroma through the endothelium, the dashed line shows the flow by pumping from the stroma to the aqueous humor through the endothelium and semi-dashed line shows the flow by diffusion of tears to the stroma through the epithelium.
Figure 2:
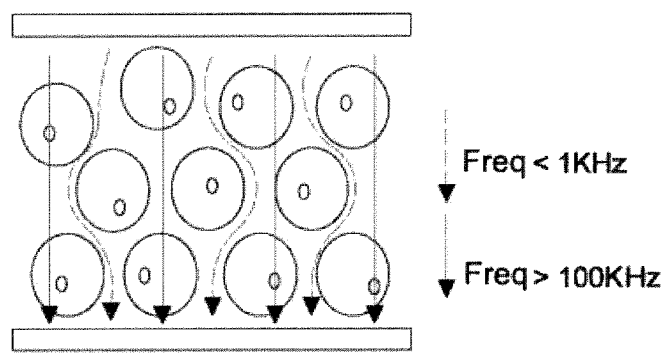
FIG. 2 schematically shows the behavior of the electric current at different frequencies when passing through cell layers. The dashed lines represent low frequencies, <1 kHz, and it is observed that the current is distributed in the extra-cellular medium. Solid lines show high frequencies, >100 kHz, and it is observed that the current flows through the cell wall and the intracellular medium.
Figure 3A:
FIG. 3A shows a diagram of the different layers defining the sensor, the substrate and the microelectrodes.
Figure 3B:
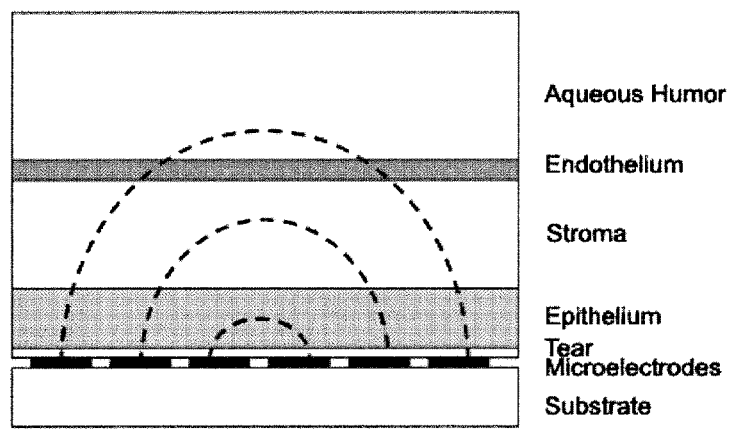
FIG. 3B illustrates how the use of the same sensor by conveniently combining microelectrodes from the several microelectrodes present in the sensor, allows the penetration of the current to the different layers of the cornea.
Figure 4:
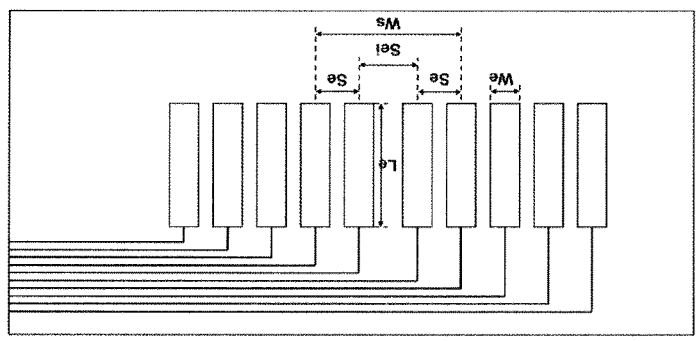
FIG. 4 shows an example of a sensor with 10 microelectrodes, where the different parameters of the geometry of the sensor are defined: We, width of the microelectrode; Le; length of the microelectrode; Ws, width of microelectrode assembly selected for taking measurement; Se, distance between the middle lines of an internal microelectrode and the closest external microelectrode; Sei, distance between the middle lines of the internal microelectrodes.
Figure 5:
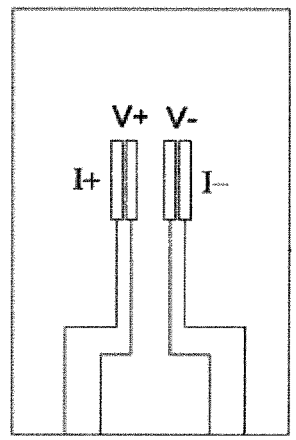
FIG. 5 shows an example of a sensor formed by four microelectrodes arranged on a substrate, detailing the two external microelectrodes (I+, I−) and the two internal microelectrodes (V+, V−) for a four-point impedance measurement.

A preferred embodiment of the device object of the invention is described below with reference to the attached drawings.

In this example a sensor with 10 microelectrodes made of gold deposited on a glass substrate was used. To prevent the tracks from making electrical contact with the cornea, these were covered by an insulating layer of $SiO_2$—$Si_3N_4$ (300 nm+700 nm). The shape of the microelectrodes and the insulating layer was made by means of photolithography methods standard in micro technology methods.

The correlation between impedance measurements of the cornea and the functionality of the different layers of the cornea were validated by means of experimental tests in rabbits. Therefore, functional alterations were induced in the cornea by means of administrating benzalkonium chloride (BAC) diluted to 0.05% by volume. This compound disrupts the junctions between the cells causing an increased permeability of the corneal layers.

In order to detect alterations in the epithelial layer a configuration of microelectrodes with a Ws of 1 mm and a Nre of 3 was selected. The impedance equipment injected a current of 10 μA at 100 Hz between the external microelectrodes and recorded the potential drop in the internal microelectrodes, the impedance measurement of the cornea being obtained. The measurement obtained at 100 Hz was 10 KΩ±2 KΩ in the case of a healthy cornea and 4 KΩ±1 KΩ in the case of a cornea with an altered epithelial layer. Repeating the same method, in order to detect alterations in the endothelial layer a configuration of microelectrodes with a Ws of 5 mm and a Nre of 3 was selected, a measurement of 2 KΩ±0.5 KΩ for a healthy cornea and a measurement of 200 Ω±100Ω for a cornea with an altered endothelial layer being obtained at 10 kHz. Following the same experimental method the increase in stromal hydration due to the increase in the corneal endothelium permeability was measured. To that end, a configuration of microelectrodes with a Ws of 1.8 mm and a Nre of 3 was selected, a measurement of 250 Ω±20Ω for a healthy cornea and a measurement of 80 Ω±20Ω for a cornea with an altered stromal layer being obtained at 1 MHz.

The invention claimed is:

1. A sensor for measuring impedance comprising n microelectrodes, wherein n is between 4 and 30, arranged on a substrate, the size and arrangement of the microelectrodes being suitable so that the contact a cornea simultaneously, and wherein the microelectrodes are selected for taking measurement in groups of 4 by way of 2 external microelectrodes and 2 internal microelectrodes, wherein the microelectrodes have an elongated shape, so as to have a length and a width, and are arranged in parallel according to their longest side, and wherein the sensor comprises 10 microelectrodes.

2. The sensor for measuring impedance according to claim 1, wherein the width of an electrode assembly formed by the microelectrodes selected for taking the measurement is, or the distance between the middle lines of the external microelectrodes Ws is, between 0.2 mm and 11 mm.

3. A sensor for measuring impedance comprising n microelectrodes, wherein n is between 4 and 30, arranged on a substrate, the size and arrangement of the microelectrodes being suitable so that they contact a cornea simultaneously, and wherein the microelectrodes are selected for taking measurement in groups of 4 by way of 2 external microelectrodes and 2 internal microelectrodes, wherein the microelectrodes have an elongated shape, so as to have a length and a width, and are arranged in parallel according to their longest side, and wherein the width of an electrode assembly formed by the microelectrodes selected for taking the measurement is, or the distance between the middle lines of the external microelectrodes Ws is, 1 mm in the case of epithelium, 1.8 mm in the case of stroma or 5 mm in the case of endothelial layer.

4. The sensor for measuring impedance according to claim 3, wherein the microelectrodes are made of metal material that is gold, platinum, nickel, aluminum, titanium, titanium nitride, chromium or alloys thereof.

5. The sensor for measuring impedance according to claim 3, wherein the microelectrodes are made of non-metal material that is carbon nanotubes, graphene or conductive polymers.

6. The sensor for measuring impedance according to claim 3, wherein the width of each microelectrode We is between 0.03 mm and 1 mm.

7. The sensor for measuring impedance according to claim 6, wherein the width of each microelectrode We is 0.3 mm.

8. The sensor for measuring impedance according to claim 3, wherein the length of the microelectrode Le is between 0.03 mm and 11 mm.

9. The sensor for measuring impedance according to claim 8, wherein the length of the microelectrode Le is 1 mm or 2 mm.

10. The sensor for measuring impedance according to claim 3, wherein the ratio of microelectrode gap Nre=Sei/Se, wherein Sei is the distance between the middle lines of the internal microelectrodes and Se is the distance between the middle lines of an internal microelectrode and the closest external microelectrode, is between 0.1 and 20.

11. The sensor for measuring impedance according to claim 3, wherein the substrate on which the microelectrodes are arranged is rigid and is made of silicon, silicon carbide, glass or PCB (printed circuit board, RF4), and is optionally transparent.

12. The sensor for measuring impedance according to claim 11, wherein the microelectrodes are 2 mm in length and 0.3 mm in width.

13. The sensor for measuring impedance according to claim 3, wherein the substrate on which the microelectrodes are arranged is flexible and is made of SU8, polymethylmethacrylate (PMMA), polydimethylsiloxane (PDMS), polyimide, polyethylene naphthalate (PEN), polyethylene terephthalate (PET), polystyrene, cycloolefin polymer (COP) or polycarbonate, and is optionally transparent.

14. The sensor for measuring impedance according to claim 13, wherein the microelectrodes are 1 mm in length and 0.3 mm in width.

15. The sensor for measuring impedance according to claim 3, wherein the microelectrodes are arranged in a planar manner on the substrate, or wherein the sensor is made in a lens shape, adapted to a support or adapted to a container that can contain isolated corneas.

16. A sensor for measuring impedance comprising n microelectrodes, wherein n is between 4 and 30, arranged on a substrate, the size and arrangement of the microelectrodes being suitable so that they contact a cornea simultaneously, and wherein the microelectrodes are selected for taking measurement in groups of 4 by way of 2 external microelectrodes and 2 internal microelectrodes, wherein the microelectrodes have an elongated shape, so as to have a length and a width, and are arranged in parallel according to their longest side, wherein the ratio of microelectrode gap Nre=Sei/Se, wherein Sei is the distance between the middle lines of the internal microelectrodes and Se is the distance between the middle lines of an internal microelectrode and the closest external microelectrode is 3.

17. A device for measuring impedance comprising:
 a sensor for measuring impedance comprising n microelectrodes, wherein n is between 4 and 30, arranged on a substrate, the size and arrangement of the microelectrodes being suitable so that they contact a cornea simultaneously, and wherein the microelectrodes are selected for taking measurement in groups of 4 by way of 2 external microelectrodes and 2 internal microelectrodes, wherein the microelectrodes have an elongated shape, so as to have a length and a width, and are arranged in parallel according to their longest side, and
 a multi-frequency impedance measuring equipment connected to the sensor.

18. A method for measuring impedance to determine the functional characteristics of the cornea comprising examining the cornea with a sensor comprising between 4 and 30 microelectrodes arranged on a substrate so as to contact the cornea simultaneously, and determining the functional characteristics of the cornea by taking measurement from the microelectrodes in groups of 4 of which 2 are external microelectrodes and 2 are internal microelectrodes, wherein each of the microelectrodes makes direct electrical contact with the cornea, wherein the width of an electrode assembly formed by the microelectrodes selected for taking the measurement Ws is less than 1.5 mm and the frequency at which the measurement is taken is less than 1 kHz in the case of epithelium, or wherein the width of the selected electrode assembly Ws is greater than 3 mm and the frequency at which the measurement is taken is comprised between 1 kHz and 100 kHz in the case of endothelium, or wherein the width of the selected electrode assembly Ws is comprised between 1.5 mm and 3 mm and the frequency at which the measurement is taken is greater than 100 kHz in the case of stroma.

* * * * *